United States Patent
Veatch

[19]

[11] Patent Number: 6,010,536
[45] Date of Patent: Jan. 4, 2000

[54] LOW-ENERGY SEQUENTIAL-ACTION PREHENSOR

[76] Inventor: Bradley D. Veatch, 2514 W. 104th Cir., Westminster, Colo. 80234

[21] Appl. No.: 08/924,762

[22] Filed: Aug. 27, 1997

[51] Int. Cl.[7] ..................................................... A61P 2/54
[52] U.S. Cl. ................................... 623/63; 414/6; 901/31
[58] Field of Search ................................ 623/63, 64, 57, 623/58, 59; 414/5, 7; 901/31, 39; 294/28, 902, 164

[56] References Cited

U.S. PATENT DOCUMENTS

| | | | |
|---|---|---|---|
| 1,981,698 | 11/1934 | Henning | 623/64 |
| 2,382,403 | 8/1945 | Eberle | 623/63 |
| 2,409,884 | 10/1946 | Mollenhour | 623/63 |
| 2,641,769 | 6/1953 | Robinson | 623/64 |
| 3,604,017 | 9/1971 | Brown et al. | 3/12.7 |
| 4,225,983 | 10/1980 | Radocy et al. | 3/12 |
| 4,332,038 | 6/1982 | Freeland | 3/12.6 |
| 4,377,305 | 3/1983 | Horvath | 623/64 |
| 4,792,338 | 12/1988 | Rennerfelt | 623/64 |
| 4,923,477 | 5/1990 | Horvath | 623/57 |
| 4,990,162 | 2/1991 | Leblanc et al. | 623/63 |
| 5,116,386 | 5/1992 | Scribner | 623/64 |
| 5,219,366 | 6/1993 | Scribner | 623/57 |

FOREIGN PATENT DOCUMENTS

| | | | |
|---|---|---|---|
| 488300 | 9/1918 | France | 623/57 |
| 126457 | 5/1919 | United Kingdom | 623/57 |

*Primary Examiner*—Mickey Yu
*Assistant Examiner*—Bruce E. Snow
*Attorney, Agent, or Firm*—Chrisman, Bynum & Johnson

[57] ABSTRACT

A voluntary close mechanical grasping device suitable for use in robotics or as a prehensor for body-power prosthetic equipment provides an energy efficient two stage process for sizing and gripping an object and a holding assist capability for assisting a wearer in maintaining his or her grip on the object. During the first stage, the device sizes an object but does not apply a force against the object sufficient to grasp the object securely. During the second stage, the device exerts a force against the object sufficient to grasp the object securely. After the object has been grasped, the device provides a mechanical holding assist capability to help hold the object securely while the input energy supplied by the wearer is reduced.

32 Claims, 10 Drawing Sheets

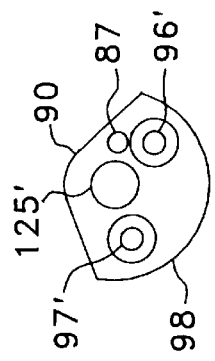
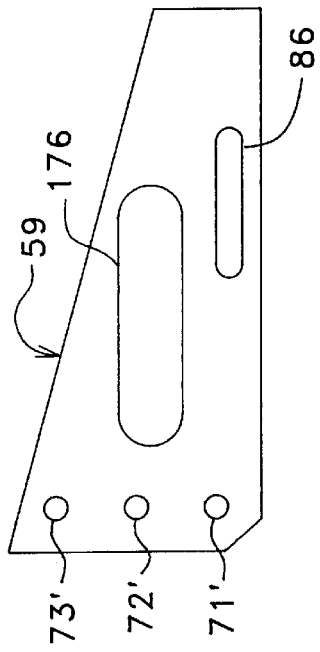
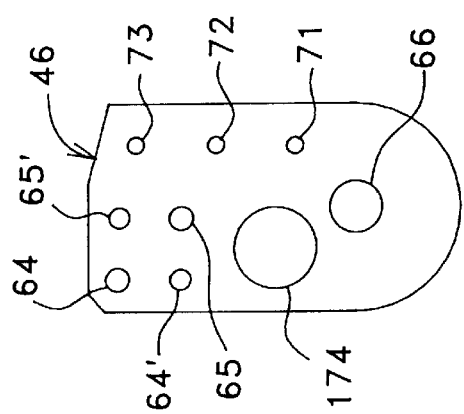
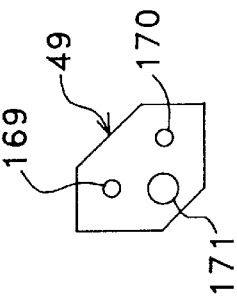
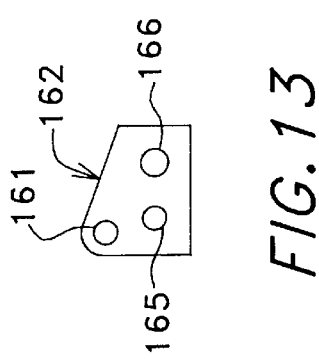
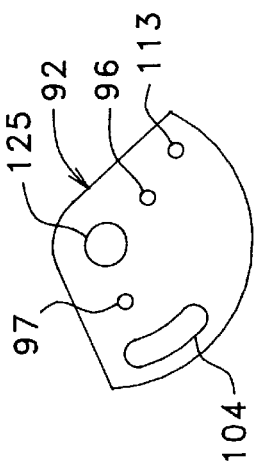

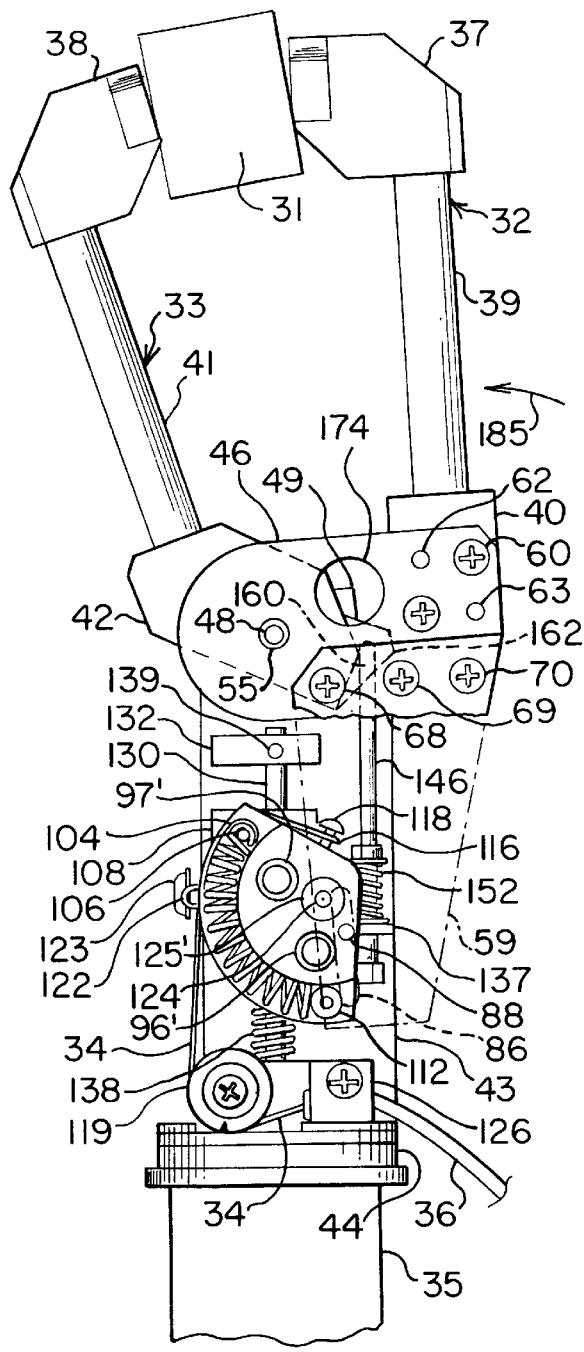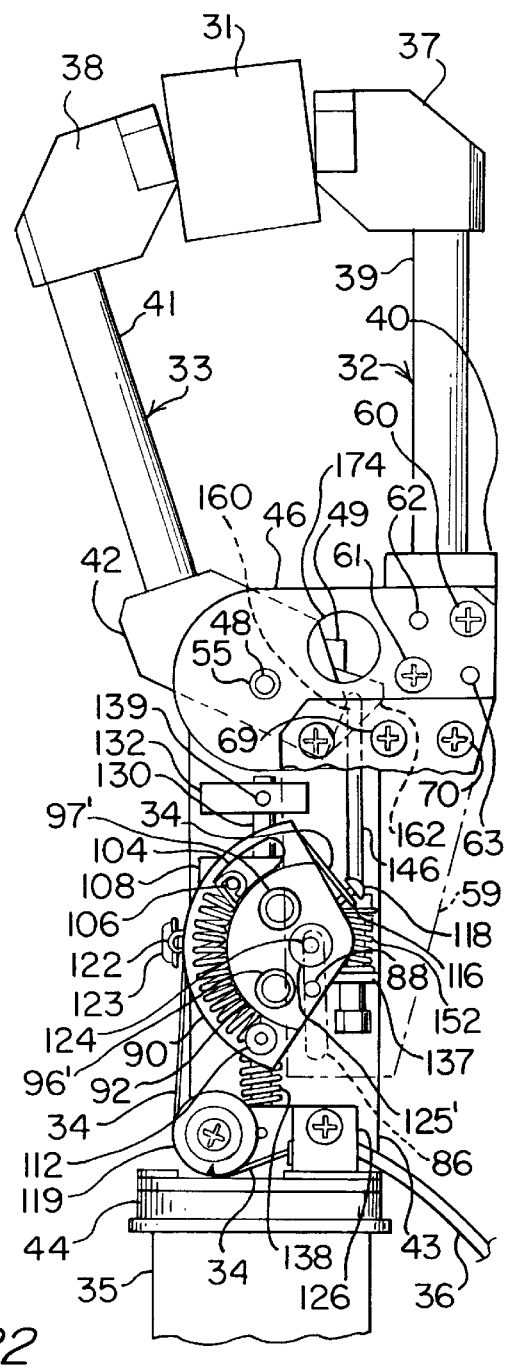
FIG. 21
FIG. 22

LOW-ENERGY SEQUENTIAL-ACTION PREHENSOR

BACKGROUND OF THE INVENTION

1. Field of the Invention

This invention relates generally to a prehensor and, more specifically, to a voluntary close prehensor that sequentially varies the ratio of input control cable tensile force to actual gripping force to obtain energy-efficient mechanical advantage during gripping.

2. Description of the Prior Art

In the United States, approximately 90,000 individuals are considered to be upper-body amputees, having lost all or a portion of an upper limb. Of those, a subset will use a prosthetic (artificial) arm to enhance or restore their capabilities and, hopefully, their quality of life. While a number of prosthetic devices have been developed to assist these individuals, their use is not wide-spread due, at least in part, to the poor performance and design of existing prosthetics and prehensors. A prehensor, also known as a "gripper" or an "end-effector," is a mechanical grasping device used by an upper-body amputee to serve as an artificial hand.

In response to the need for prosthetic arms and associated prehensors, two types of devices have been developed and marketed: battery-powered electronic systems and body-powered mechanical systems. Electronic systems using a battery package, electric motors, and sophisticated electronic controls have been developed and shown to work reasonably well. Unfortunately, electronic systems are very expensive, often costing $35,000 or more for entry models. In addition, electronic systems can be unrealistically heavy and suffer from inadequate battery life. U.S. Pat. No. 4,792,338 issued to Rennerfelt discloses an electronic or battery-powered prehensor.

The second type of prosthetic devices commonly used are called "body-powered" systems" because the wearer controls the system using muscles in his or her body, usually muscles in the shoulder and neck. Body-powered mechanical systems are generally lighter, quieter, and far less expensive than their electronic counterparts, and do not suffer from battery-life limitations.

Within the realm of body-powered prosthetics, there are two primary families, differing primarily in the type of prehensor used. Voluntary open (VO) prehensors typically include two or more gripping digits (mechanical fingers with rubber pads for friction and better grip) that are held or biased against each other by a spring or one or more strong rubber bands. The wearer moves the digits apart prior to gripping by pulling on a control cable connected to the wearer's shoulder and neck through a harness. When the wearer relaxes or eases the tension on the control cable, the digits close on the object to be held and "grip" it. In essence, voluntary open prehensors are spring loaded clamps that can be opened at will by the wearer. Therefore, with a voluntary open prehensor, the wearer's grip on the object is passive and the wearer need do nothing to maintain the grip.

Voluntary open prehensors are popular due to their low cost as compared to electronic prehensors, and the fact that the wearer does not expend energy while gripping an object. Unfortunately, since gripping an object with a voluntary open prehensor is passive, i.e., the wearer is not expending energy to maintain the grip, the wearer has limited, if any, control over the amount of force exerted on the object. Gripping forces needed to lift heavy objects are excessive for small or lightweight fragile objects. Conversely, the correct gripping force needed to lift a light object will usually be inadequate for heavier objects. U.S. Pat. No. 3,604,017 issued to Brown et al. and U.S. Pat. No. 5,116,386 issued to Scribner disclose voluntary open prehensors.

The second major type of body-powered prehensors are the voluntary close (VC) prehensors. As its name implies, unlike a voluntary open prehensor, the gripping digits in a voluntary close prehensor are closed upon an object to be grasped by actively exerting force on a control cable attached to the wearer's shoulder and neck using a harness. Voluntary close prehensors offer several important advantages over voluntary open prehensors. First, a voluntary close prehensor is more physiologically intuitive than a voluntary open prehensor. That is, a voluntary close prehensor requires a wearer to exert muscular force to grasp and hold an object while a voluntary open prehensor requires the wearer to relax his or her muscles to initiate and maintain a grip. Second, in a voluntary close prehensor, the gripping force applied to the object to be grasped by the wearer is directly related to the force the wearer exerts on the control cable. Requiring the wearer to exert force when grasping an object provides feedback to the wearer, thereby giving the wearer a sense of how strong his or her grip is upon the object. This feedback, also called physiological proprioception, allows the voluntary close prehensor to become an extension of the wearer's body with a natural feel and a confident grasp. Since voluntary open prehensors do not provide this feedback, the wearer is effectively removed from the gripping cycle. Third, by requiring that the wearer only exert the amount of energy necessary to attain the gripping force required to grasp an object, voluntary close prehensors conserve a large amount of the wearer's energy. In contrast, voluntary open prehensors require the wearer to stretch springs or rubber bands to separate or open the digits each time grip is to be applied to an object, regardless of the size or weight of the object. Any excess energy used to open the digits is wasted.

While voluntary close prehensors are generally more energy efficient that voluntary open prehensors, voluntary close prehensors still require the wearer to exert significant energy while maintaining a grasp on an object. Therefore, wearers desire voluntary close prehensors that reduce the energy needed to grasp an object as much as possible while providing feedback as to the force the wearer is exerting against the object. Many types of voluntary close prehensors are known in the prior art. For example, U.S. Pat. No. 4,225,983 issued to Radocy et al. and U.S. Pat. No. 4,332,038 issued to Freeland both disclose voluntary close prehensors. Radocy et al. focus their prehensor design towards achieving optimally configured gripping surfaces for the prehensor that can be inexpensively manufactured using stamped plate construction techniques. While Radocy et al. provide a locking pawl to assist the wearer in maintaining a grip on an object, unfortunately, Radocy et al. require that the wearer manually actuate the locking pawl. Freeland discloses an artificial hand with a pivotal thumb to adapt the hand for gripping different objects. Unfortunately, Freeland does not provide an energy efficient device capable of assisting a wearer in maintaining a grip on an object.

Despite the well developed state of the prior art, there remains a need for a voluntary close prehensor that conserves the energy expended by the wearer to size and grip an object. Preferably, the voluntary close prehensor will mechanically assist a wearer in maintaining the grip on the object without requiring any additional manual intervention by the wearer.

SUMMARY OF THE INVENTION

A general object of the present invention is to provide a voluntary close prehensor.

Another general object of the present invention is to provide a prehensor that assists in maintaining an applied gripping force.

It is another general object of the present invention to provide a prehensor that enables physiological prociprioception for the wearer of the prehensor.

Yet another general object of the present invention is to provide a prehensor capable of efficiently adjusting its applied gripping force.

Still another general object of the present invention is to provide a prehensor that efficiently sizes the grip necessary to hold or clasp an item.

A further general object of the present invention is to provide a prehensor that conserves energy while maintaining a grip on an item.

Another general object of the present invention is to provide a prehensor capable of use with an amputee or a robot.

Additional objects, advantages, and novel features of the invention shall be set forth in part in the description that follows, and in part will become apparent to those skilled in the art upon examination of the following or may be learned by the practice of the invention. The objects and the advantages may be realized and attained by means of the instrumentalities and in combinations particularly pointed out in the appended claims.

To achieve the foregoing and other objects and in accordance with the purposes of the present invention, as embodied and broadly described herein, the prehensor preferably includes a cable, a sizing digit pivotable or rotatable about a shaft, a gripping digit assembly pivotable or rotatable about the same or a different shaft, a carriage block slidable along a lock rod, a spring biased lock plate coupled to the sizing digit via a linkage rod and slidable along the lock rod and skewable or tiltable about the lock rod such that neither the carriage block nor the lock plate are slidable along the lock rod when the lock plate is skewed about the lock rod, a rotatable cam plate assembly connected to the cable and the carriage block and coupled to the gripping digit assembly.

During gripping of an object with the prehensor, as tension in the cable is increased, the carriage block and the lock plate will slide along the lock rod, thereby causing rotation of the sizing digit, until the object comes into contact with the sizing digit and the gripping digit assembly. Upon contact of the object with the sizing digit and the gripping digit assembly, the lock plate will become skewed about the lock rod, thereby preventing the carriage block and the lock plate from sliding any further along the lock rod. An increase in cable tension after the lock plate has skewed about the lock plate will cause rotation of the cam plate assembly such that the gripping digit assembly rotates to apply a grasping force on the object.

The prehensor preferably includes an optional clutch drum around which the cable is wound to provide a holding assist. The clutch drum rotates when the cable tension is increased but does not rotate when the cable tension is decreased, thereby assisting in maintaining a sufficient grasp on the object.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

In the Drawings:

FIG. 6 illustrates an elevation view of one of the grip digit plates of the prehensor of FIG. 1;

FIG. 7 illustrates an elevation view of the cam lever plate of the prehensor of FIG. 1;

FIG. 8 illustrates an elevation view of the upper cam plate of the prehensor of FIG. 1;

FIG. 9 illustrates an elevation view of the lower cam plate of the prehensor of FIG. 1;

FIG. 13 illustrates an elevation view of the sizing block lever tab of the prehensor of FIG. 1;

FIG. 14 illustrates an elevation view of the shaft support plate of the prehensor of FIG. 1;

FIG. 21 illustrates a side elevation view of the prehensor of FIG. 1, with the prehensor shown fully gripping an object; and FIG. 22 illustrates a side elevation view of the prehensor of FIG. 1, with the prehensor shown releasing its grip on the object.

DETAILED DESCRIPTION OF THE PREFERRED EMBODIMENTS

Figure 1:
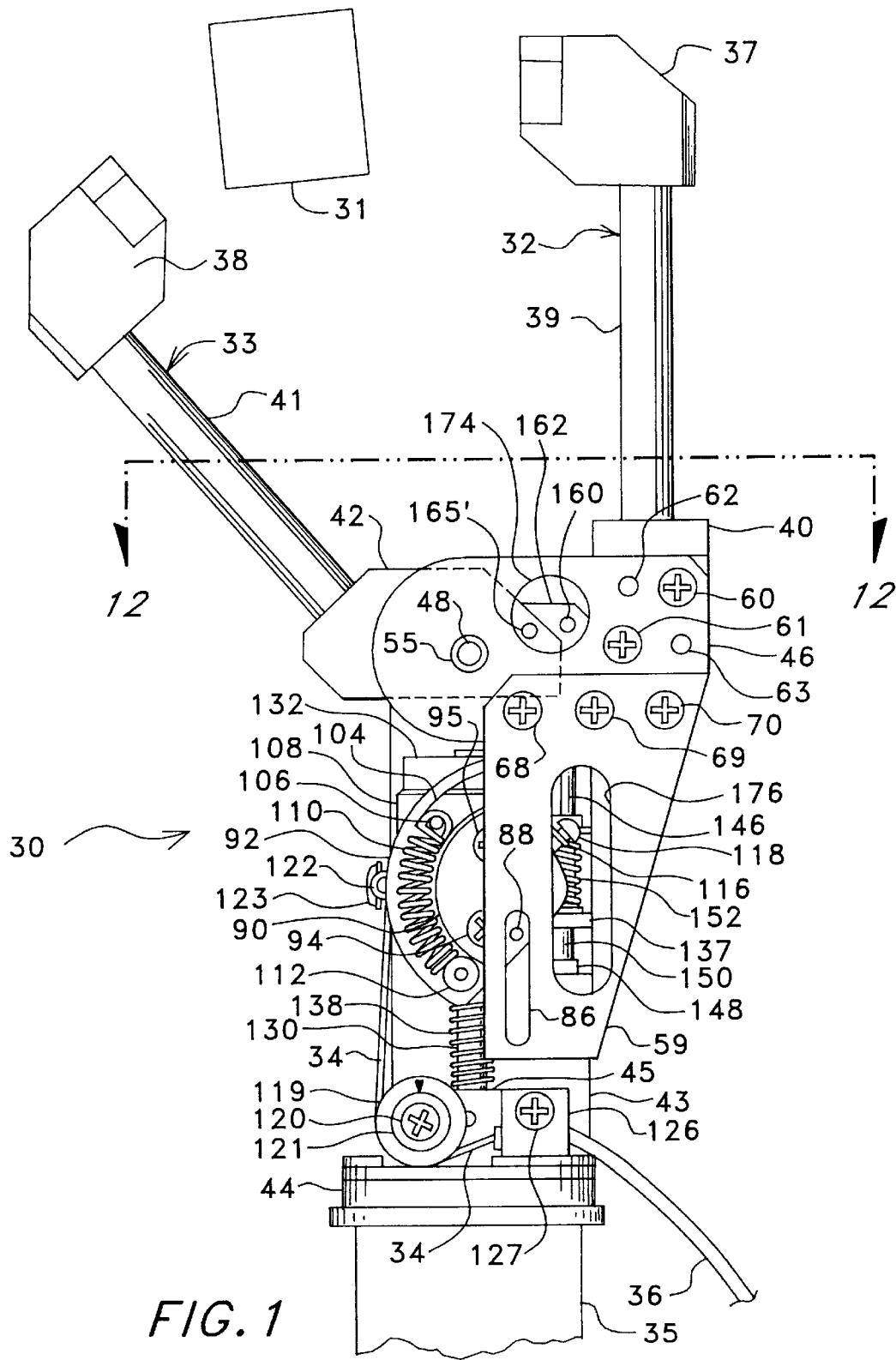
FIG. 1 illustrates a side elevation view of the voluntary close prehensor of the present invention, with the prehensor shown in its fully open position.
Figure 2:
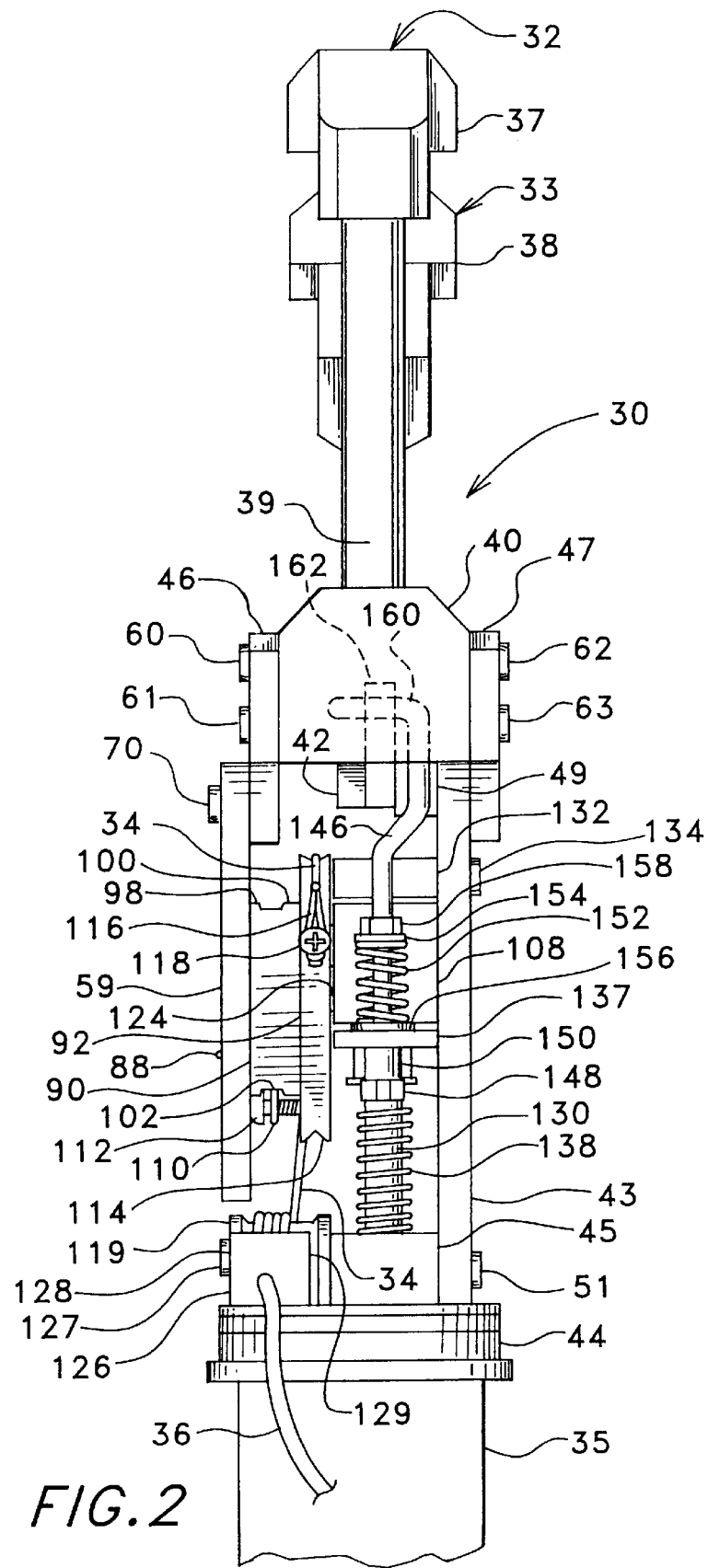
FIG. 2 illustrates a top plan view of the prehensor of FIG. 1.

The prehensor 30 of the present invention is illustrated in FIGS. 1 and 2 in its fully open position in preparation for grasping or gripping an object, such as the object 31. The prehensor 30 includes a rotatable gripping digit 32 and a rotatable sizing digit 33 for gripping or grasping the object 31 and a cable 34 preferably attached to a harness (not shown) worn around a wearer's neck and torso for controlling the movement of the digits 32, 33 and the force exerted against the object 31 with the digits 32, 33. The prehensor 30 is preferably attached via a mounting boss, stud, or handle 35 to a wearer's arm, or a prosthetic, robotic, or other device. The boss 35 can be threaded or unthreaded. The mounting of a prehensor to a boss, or a prosthetic, robotic, or other device is well known to people of ordinary skill in this art and does not form the basis of the present invention. Therefore, no further discussion of the boss 35 or how the prehensor 30 is attached to a harness or to a prosthetic or robotic device is required for purposes of explanation of the present invention.

Significant features of the prehensor 30 of the present invention include: first, the mechanical control of the digits 32, 33 via the cable 34, which may be located within a protective sheave 36, and other intermediary mechanical components to provide energy efficient sizing and gripping or grasping of an object, such as the object 31, with the digits 32, 33 and, second, the mechanical assistance provided to the wearer to maintain a grip on the object after the object has been grasped with the digits 32, 33, thereby reducing the energy required from the wearer to maintain a grip on the object. In order to complete a grip on an object, such as the object 31, with the prehensor 30, the prehensor 30 uses essentially a two step process. First, the prehensor 30 "sizes" to fit the object by creating movement, rotation, or pivoting of the sizing digit 33 relative to the gripping digit 32 until the digit blocks 37, 38 on the digits 32, 33, respectively, contact the object. The "sizing" of an object refers to moving the digit blocks 37, 38 together until the digit blocks 37, 38 just fit around or just contact the object and exert little, if any, force against the object. Since during this first stage of the grip process with the prehensor 30, very little, if any, force is exerted against the object, the wearer exerts little force against the object and expends less energy in comparison to the second stage of the grip process. During the second stage of the grip process with the prehensor 30, the gripping digit 32 generally moves, rotates, or pivots relative to the sizing digit 33 to apply a gripping force to the object and hold the object securely between the digits 32, 33 and, more specifically, between the digit blocks 37, 38. After the wearer has gripped an object between the digit blocks 37, 38, the prehensor 30 assists the wearer in maintaining a gripping force against the object with the digit blocks 37, 38, thereby allowing the wearer to relax the tension exerted by the wearer via the cable 34 on the digits 32, 33. While the tension in the cable 34 supplied by the wearer is relaxed, the prehensor 30 maintains a tension on the cable 34 with a holding assist feature sufficient to maintain a grasp of the object. These and other significant advantages of the prehensor 30 and the gripping process of the prehensor 30 will be discussed in more detail below. While the prehensor 30 is illustrated and described as a voluntary close type prehensor, the concepts embodied in the prehensor of the present invention will also work in large part with a voluntary open type prehensor.

Before discussing the operation of the prehensor 30, the components of the prehensor 30 will first be discussed in more detail. Referring again to FIGS. 1 and 2, the gripping digit 32 includes a rod 39 connecting the digit block 37 to grip block 40. The digit block 37 is mounted or otherwise attached to an end of the rod 39 while the opposite end of the rod 39 is attached to the grip block 40. Similarly, the sizing digit 33 includes a rod 41 connecting the digit block 38 to rotatable size block 42 such that the digit block 38 is mounted or otherwise attached to an end of the rod 41 while the opposite end of the rod 41 is attached to the size block 42. In essence, the gripping digit 32 includes the rod 39, the digit block 37, and the grip block 40 while the sizing digit 33 includes the rod 41, the digit block 38, and the size block 42. Either the gripping digit 32 or the sizing digit 33 or both can have different configurations and be optimized for different applications.

Figure 3:
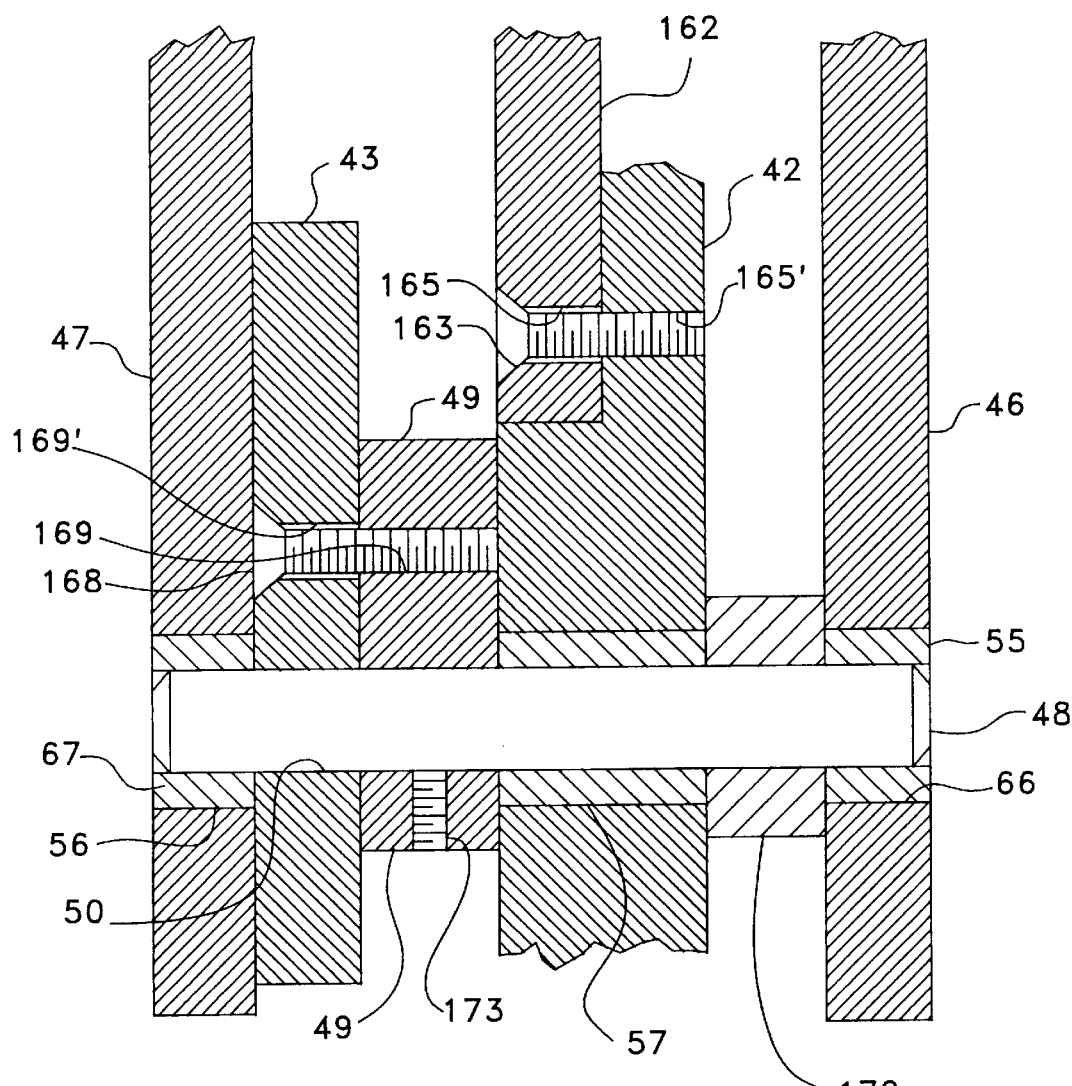
FIG. 3 illustrates an enlarged and simplified cross-sectional view of the pivot plates, main structural plate, size block, tab lever plate, shaft support plate, spacer, and bushings located along a shaft in the prehensor of FIG. 1.

The prehensor 30 includes a main structural plate 43 rigidly connected to a circular end plate 44 via the rod block 45. That is, the main structural plate 43 is bolted to the rod block 45 which is, in turn, bolted to the circular end plate 44. The circular plate 44 is rigidly connected to the boss 35. Grip pivot plates 46, 47 are preferably rigidly connected to opposite sides of the grip block 40 such that they rotate about a shaft 48 when the size block 42 rotates about the shaft 48. The size block 42 is also rotatably connected to the shaft 48. The shaft 48 extends through the size block 42, grip pivot plates 46, 47, the main structural plate 43, and the shaft support plate 49, as best illustrated in FIG. 3. Note that FIG. 3 is not meant to show all of the plates or blocks of the prehensor 30 or to be an exact representation of the plates and blocks of the prehensor 30. Rather, FIG. 3 provides a simplified and enlarged illustration of the components of the prehensor 30 that are connected to the shaft 48 and the relative positioning of those components along the shaft 48 and to each other.

Figure 5:
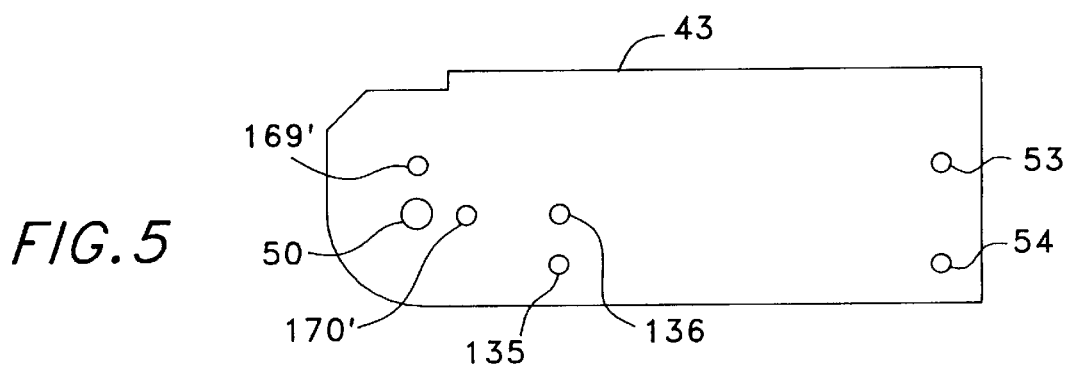
FIG. 5 illustrates an elevation view of the main structural plate of the prehensor of FIG. 1.

The shaft 48 extends through the bore 50 in the plate 43. The main structural plate 43 is rigidly attached to the rod block 45 via bolts 51 and 52 (see FIG. 4) that extend through bores 53, 54, respectively, (see FIG. 5) in the main structural plate 43 and into the rod block 45. The rod block 45 is rigidly attached to a circular end plate 44. Bushings 55, 56, and 57 separate the pivot plates 46, 47 and the size block 42, respectively, from the shaft 48 such that the shaft 48 does not directly contact the pivot plates 46, 47 or the size block 42. Rather, the shaft 48 preferably rotates inside the bushings 55, 56, 57 to prevent galling between the shaft 48 and the pivot plates 46, 47 and the size block 42. The cam lever plate 59 is rigidly attached to the pivot plate 46. All of these plates and blocks will be discussed in more detail below. The plates 43, 46, 47, and the blocks 40, 42, 45 preferably comprise steel or aluminum, but can comprise other metals and other materials as well.

The grip block 40 is securely attached via eternally threaded bolts 60, 61, 62, 63 to grip digit pivot plates 46, 47. The pivot plates 46, 47 preferably have identical shapes, such as the shape indicated in FIG. 6 for the plate 46. In addition, the pivot plates 46, 47 are preferably both flat and rotatably connected to the shaft 48 via the bushings 55, 56, respectively. The plate 46 includes bores 64, 65 through which the bolts 60, 61, respectively, extend to attach the plate 46 to the grip block 40. The plate 46 also includes a bore 66 through with the shaft 48 and the bushing 55 extend, as best illustrated in FIGS. 3 and 6. The plate 47 includes a similar bore 67 through which the shaft 48 and the bushing 56 extend, as best illustrated in FIG. 3. The plate 47 also contains bores (not shown) similar to the bores 64', 65' in the plate 46 for attaching the plate 47 to the grip block 40 and through which the bolts 62, 63, respectively, extend.

The cam lever plate 59 is securely attached to the grip pivot plate 46 via externally threaded bolts 68, 69, 70 extending through bores 71', 72', 73', respectively, in the cam lever plate 59 and into the internally threaded bores 71, 72, and 73, in the grip pivot plate 46, as best illustrated in FIG. 7, that align with the bores 71', 72', 73', of the cam lever plate 59 respectively, when the cam lever plate 59 is attached to the pivot plate 46.

The cam lever plate 59 includes a slot 86 through which rod 88 extends. The rod 88 is rigidly connected to the bore 87 in upper cam plate 90 and extends outward from the upper cam plate 90. The upper cam plate 90 is rotatable and rigidly connected to a rotatable lower cam plate 92 via externally threaded bolts 94, 95 (see FIG. 1). The bolts 94, 95 extend through the countersunk non-threaded bores 96', 97', respectively, (see FIG. 8) in the upper cam plate 90 and into the internally threaded bores 96, 97, respectively, (see FIG. 9) in the lower cam plate 92 when the upper cam plate 92 is rigidly connected to the lower cam plate 90. Please note that the bolts 94, 95 are not shown in FIGS. 17, 19, 21, and 22 for purposes of simplification of these Figures. The upper cam plate 90 preferably has edges 98, 100 and a peripheral slot or groove 102 formed between the edges 98, 100 (see FIG. 2). The rod 88 and the cam lever plate 59 mechanically couple or link the cam plates 90, 92 and the gripping digit 32 such that rotation of the cam plates 90, 92 causes rotation of the gripping digit 32 about the shaft 48, as will be discussed in more detail below.

The lower cam plate 92 includes a slot 104 extending through the lower cam plate 92. Rod 106 extends through the slot 104 and is rigidly connected to the carriage or slide block 108. Spring 110 extends from the rod 106 to externally threaded bolt 112. The bolt 112 is rigidly connected to the lower cam plate 92 via internally threaded bore 113. The spring 110 is positioned within the peripheral slot 102 in the upper cam plate 90. As will be discussed in more detail below, counterclockwise rotation of the cam plates 90, 92 causes the spring 110 to become elongated between the rod 106 and the bolt 112. The lower cam plate 92 includes a peripheral slot or groove 114 in which a portion of the cable 34 is positioned. The cable 34 preferably comprises a material which is strong, lightweight, flexible and friction resistant. For example, a SPECTRA® material or other textile cord, NYLON®, DACRON®, metal, or woven material can be used for the cable 34. An end 116 of the cable 34 is attached to the lower cam plate 92 via the bolt 118 attached to the lower cam plate 118. The cable 34 extends around the lower cam plate 92 to a clutch drum or capstan 119.

The clutch drum 119 is rigidly connected to rod block 45 via the bolt 120 and the washer 121. As will be discussed in more detail below, the clutch drum 119 preferably rotates only in the counter-clockwise direction and cannot rotate in a clockwise direction. The cable 34 is preferably wrapped around the clutch drum 119 three to seven times before extending through the sleeve 36. In addition, a cable guard 122 attached to the carriage block 108 via a bolt 123 helps maintain the cable 34 in the proper position in the groove 114 on the lower cam plate 92. The cable 34 and the cable sheave 36 extend or pass through the cable guide block 126 which is rigidly connected to the circular end plate 44. The bolt 127 extends into an internally threaded bore in the guide block 126. When tightened, the bolt 127 tightens the cantilevered sections 128, 129 of the guide block 126 together to exert a clamping force against the sheave 36, thereby holding the sheave 36 securely in place within the guide block 126.

The upper cam plate 90 and the lower cam plate 92 are both rotatable or pivotable about a shaft 124. The shaft 124 extends through the bore 125' in the upper cam plate 90 (see FIG. 8) and though the corresponding bore 125 in the lower cam plate 92 (see FIG. 9). The shaft 124 is rigidly attached to the carriage block 108 via the bore 131 (see FIG. 10). The carriage block 108 is slidable or otherwise displaceable along lock rod 130 which extends from a slide block stop 132 to the rod block 45. The slide block stop 132 is rigidly attached to the structural plate 43 via the externally threaded bolts 133, 134. The bolts 133, 134 extend through the non-threaded bores 135, 136, respectively in the plate 43 (see FIG. 5) and into internally threaded bores (not shown) in the slide block stop 132. Note that the bolts 133, 134 do not extend to, and are not connected to, the lower cam plate 92. The slide block 132 is also rigidly attached to the lock rod 130 via a set screw 139 extending into the slide block 132 and tightening against the lock rod 130.

Figure 10:
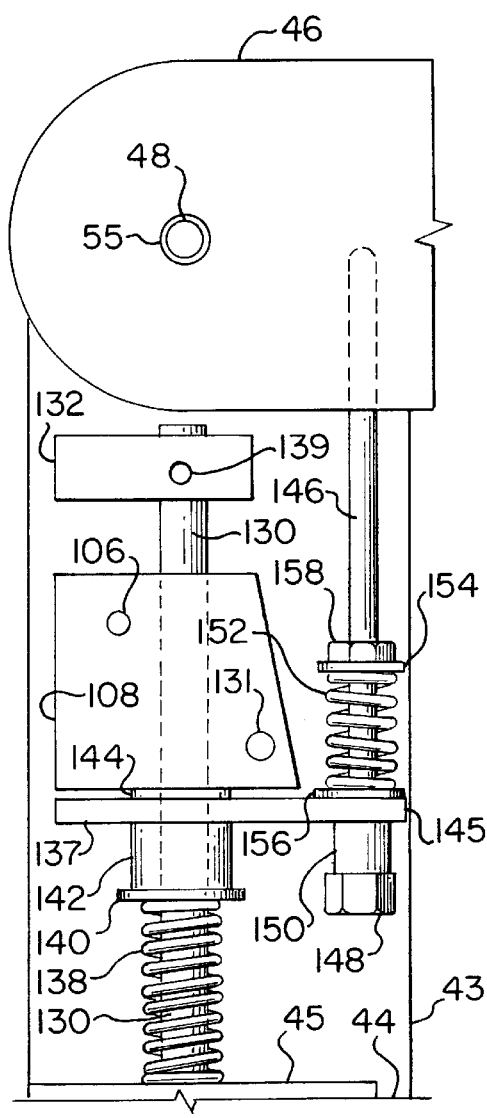
FIG. 10 illustrates an enlarged side elevation view of the size lock mechanism of the prehensor of FIG. 1, shown before the lock plate engages the lock rod while the lock plate is still square with the carriage block.
Figure 11:
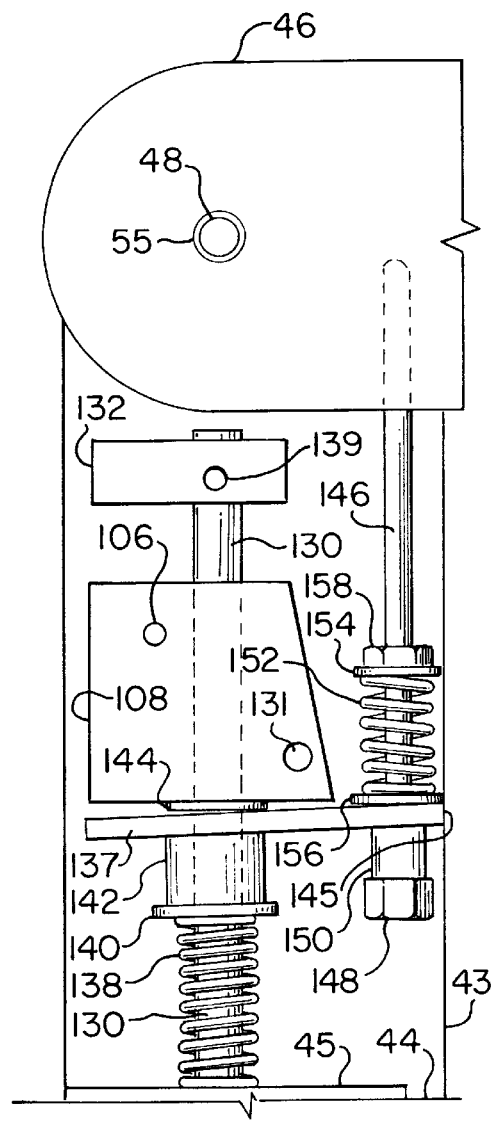
FIG. 11 illustrates an enlarged side elevation view of the size lock mechanism of FIG. 1, shown after the lock plate engages the lock rod by skewing about the lock rod.

Now referring to FIGS. 2, and 10–11, a lock plate 137 is also slidable along the lock rod 130 and tiltable or skewable about the lock rod 130. A spring 138, washer 140, and guide bushing 142 through which the lock rod 130 extends bias the lock plate 137 squarely against the carriage block 108. Preferably, a washer 144 is positioned on the lock rod 130 between the lock plate 137 and the carriage block 108 to allow clearance between the top 145 of the lock plate 137 and the carriage block 108, thereby allowing the lock plate 137 to fully skew or tilt about the lock rod 130, as will be discussed in more detail below.

A linkage rod 146 extends through the lock plate 137. A hex nut 148 and a swivel nut 150 are attached at one end of the linkage rod 146 to keep the lock plate 137 from disengaging from the linkage rod 146. As will be explained in more detail below, the lock plate 137 is tiltable or skewable about the lock rod 130 and the linkage rod 146. A spring 152 through which the linkage rod 146 extends maintains a bias against the lock plate 137 via the washers 154, 156 and the nut 158 to prevent backlash between the linkage rod 146 and the lock plate 137. Backlash is unwanted or undesirable free relative motion between the lock plate 137 and the linkage rod 146 that results in excessive, sloppy, and undesirable free play or motion of the sizing digit 33.

The linkage rod 146 and the lock plate 137 form a mechanical linkage or coupling between the carriage block 108 and the size block 42 and sizing digit 33 such that movement or displacement of the carriage block 108 along the lock rod 130 causes rotation of the sizing digit 33 about the shaft 48, as will be discussed in more detail below. The carriage block 108 and the sizing digit could be coupled or linked in other configurations.

Figure 4:
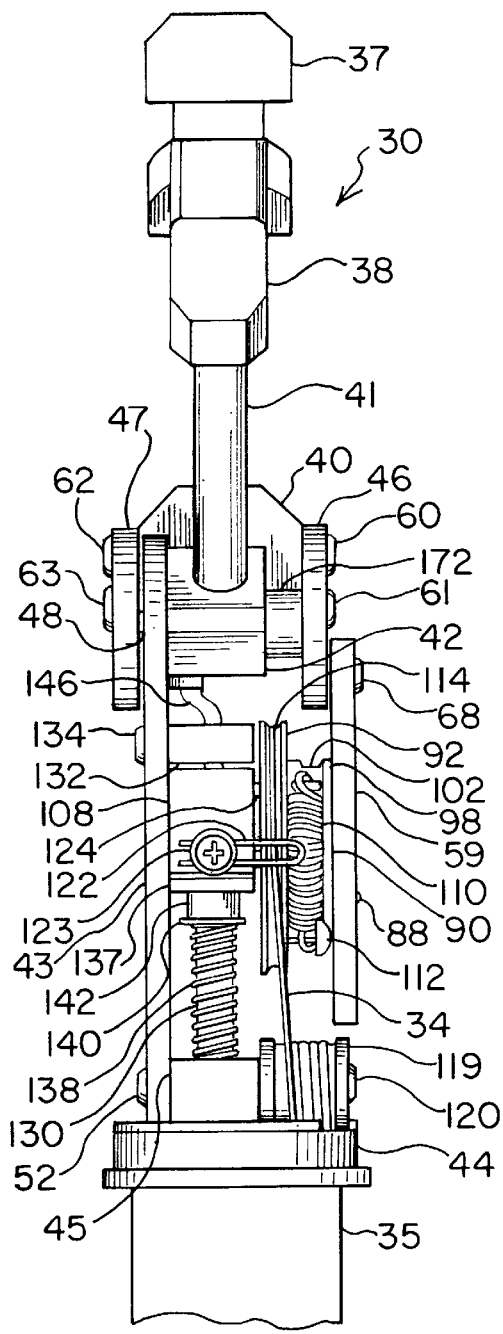
FIG. 4 illustrates a bottom plan view of the prehensor of FIG. 1.
Figure 12:
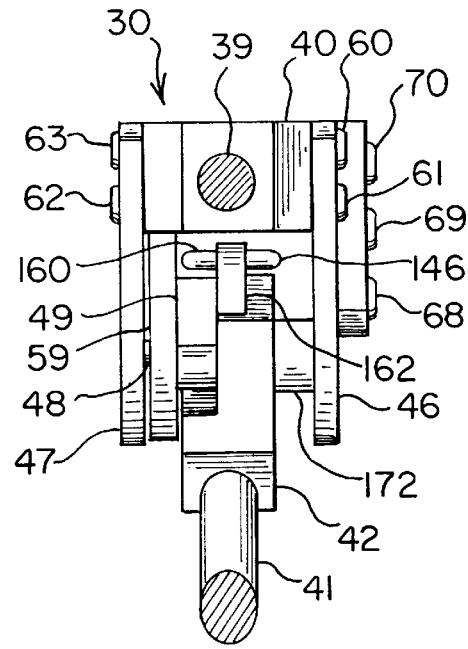
FIG. 12 illustrates an end elevation view of the prehensor of FIG. 1, taken along the line 12—12 of FIG. 1.

Now referring primarily to FIGS. 4 and 12, the linkage rod 146 extends to and is connected to the size block 42 via the sizing block lever tab or plate 162 (see FIG. 13). More specifically, the hooked end 160 of the linkage rod 146 passes through the bore 161 to connect the linkage rod 146 to the size lever plate 162. The plate 162 is rigidly connected to the size block 42 via externally threaded bolt 163 which extends through the countersunk bore 165 of the plate 162 and into the internally threaded bore 165' of the size block 42 (see FIG. 3). The size lever plate 162 also includes bore 166 through which a second externally threaded bolt (not shown) passes to furter connect the plate 162 to the size block 42. If desired, the size block 42 and the plate 162 could comprise a single piece of material. The shaft support plate 49 (see FIGS. 3 and 14) is rigidly connected to the main structural plate 43 via two externally threaded bolts (only bolt 168 is illustrated in FIG. 3) extending through bores 169', 170' in the plate 43 and into internally threaded bores 169, 170 in the plate 49. The bore 169' is countersunk to facilitate the bolt 168. The plate 49 also includes the bore 171 through which the shaft 48 extends. The plate 49 is preferably positioned between the plate 43 and the plate 162 and the size block 42 on the shaft 48. The plate 49 preferably is not connected to either the plate 162 or the size block 42 such that the plate 162 and the size block 42 can slide by the plate 49 during movement of the sizing digit 33, i.e, when the size block 42 rotates or pivots about the shaft 48, as will be discussed in more detail below.

The relative positioning of the block 42, plates 43, 46, 47, 49, along with shaft 48, spacer 172, and bushings 55, 56, and 57, is best illustrated in FIG. 3. The plate 49 is rigidly connected to the shaft 48 via a set screw (not shown) that extends into the threaded bore 173 in the plate 49 and tightens against the shaft 48 such that neither the plate 49 nor the plate 43 can rotate about the shaft 48.

The pivot plates 46, 47 can also include an optional bore or slot 174 to reduce the weight of the pivot plates 46, 47 and, as a result, to reduce the weight of the prehensor 30. Similarly, the cam lever plate 59 preferably includes an optional slot 176 which lessens the weight of the cam lever plate 59 and, as a result, the weight of the prehensor 30. The cam lever plate 59 can also include other slots or cut-out portions (not shown) to further reduce the weight of the cam lever plate 59 and the present invention should not be limited to the specific shape or design of the cam lever plate 59 illustrated in the Figures.

The operation of the prehensor 30 will now be discussed in greater detail. As previously discussed above, the prehensor 30 uses a two step process when gripping an object. First, the prehensor 30 sizes the object by moving the sizing digit 33 relative to the gripping digit 32 until the digit blocks 37, 38 on the digits 32, 33, respectively, come into contact with the object. During this first stage, very little force is exerted against the object by the prehensor 30. In fact, some force is required to be exerted against the object by the prehensor 30 to skew the lock plate 137 on the lock rod 130 after the digit blocks 37, 38 contact the object. During the second stage of the gripping process, the gripping digit 32 moves relative to the sizing digit 33 to apply a suitable gripping force on the object. Since the prehensor 30 is a voluntary close prehensor, the wearer can control the amount of force exerted against the object by controlling the tension in the cable 34.

Figure 15:
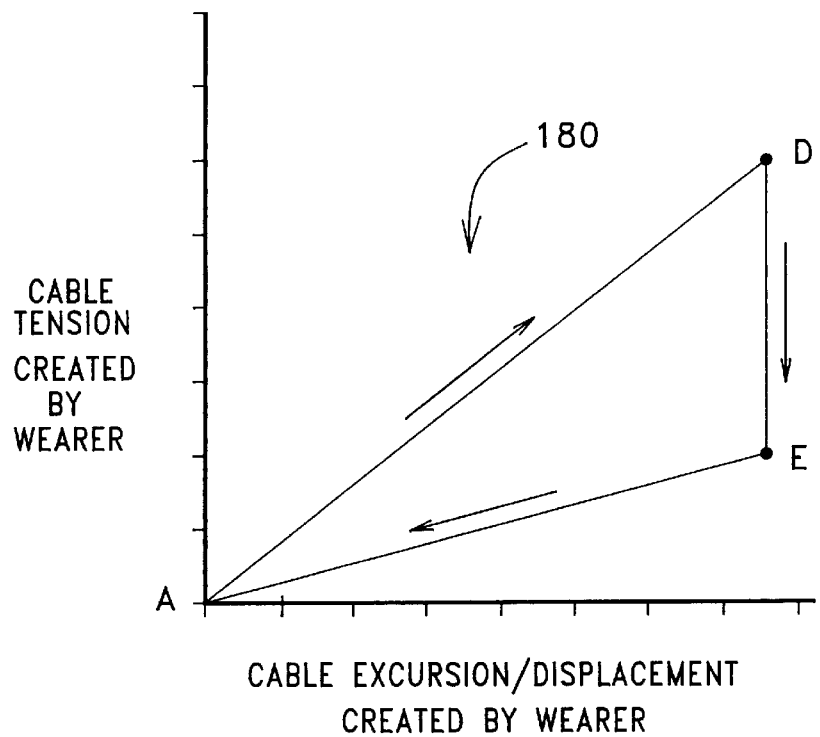
FIG. 15 illustrates a general hysteresis model of a cable tensioning system usable with the prehensor of FIG. 1.

For many cable tension actuated mechanical systems, an ideal system would require a tension in the cable proportional to the desired gripping force only upon the initial gripping of an object. After the object is gripped, the ideal system would then allow a reduced or lower tension in the cable created by the wearer to maintain the same grip force on the object. As a result, the ideal system would demonstrate hysteresis in the tension requirements, as illustrated in FIG. 15. Now referring to FIG. 15, a hypothetical hysteresis curve 180 representative of such a cable tension actuated mechanical system for a conventional voluntary close prehensor is illustrated. For this representative curve 180, cable tension is increased as the cable displacement is increased. In other words, as a cable, such as the cable 34 in the prehensor 30, is pulled, the tension in the cable is increased, thereby increasing the force exerted by the cable tension system. When the wearer creates tension in the cable to grip an object, energy is required to move the operating point of the prehensor from operating point A to operating point D. After the wearer has gripped the object with this hypothetical prehensor demonstrating hysteresis, the wearer can then relax the tension on the cable applied by the wearer without cable displacement. In other words, the prehensor maintains the same grip on the object, even though the wearer has reduced the tension applied to the cable by the wearer and the operating point of the prehensor moves from operating point D to operating point E. The prehensor supplies the needed tension to the cable to make up for the reduction in tension to the cable supplied by the wearer. Therefore, the prehensor provides assistance in maintaining grip on the object. This holding assist feature or capability of an ideal prehensor improves the prehensor's safety by passively providing make-up tension to the cable through friction instead of requiring active mechanical grabbing or clamping of the cable to prevent motion.

Figure 16:
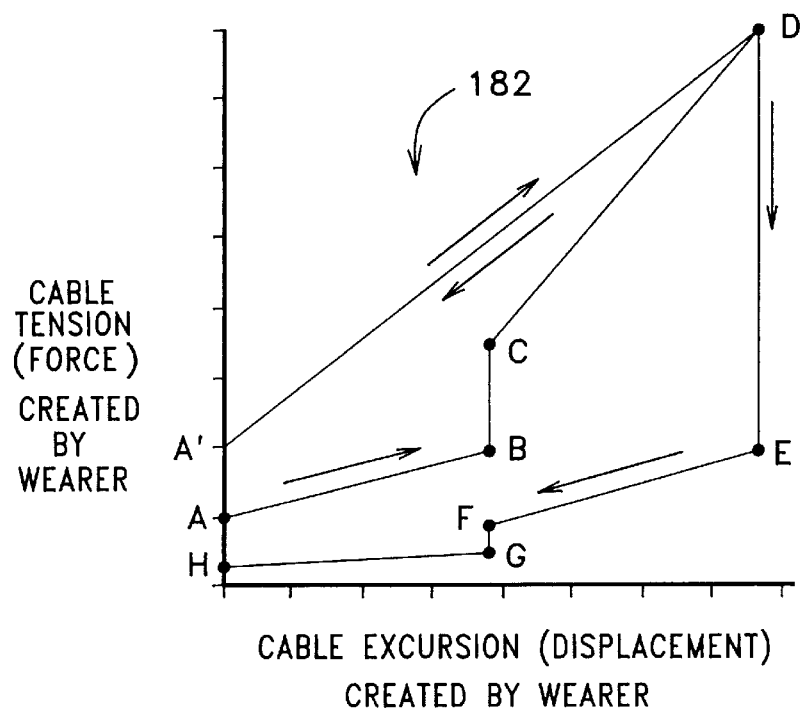
FIG. 16 illustrates an energy efficient hysteresis model of a cable tensioning system used with the prehensor of FIG. 1.

The prehensor 30 of the present invention is more closely modeled by the hysteresis curve or graph 182 illustrated in FIG. 16. As the graph 182 illustrates, the prehensor 30 demonstrates the hysteresis effect caused by having a holding assist capability which allows the wearer to reduce the tension the wearer is applying to the cable 34 while sustaining the same grip on an object. In addition, the graph 182 illustrates the prehensor's two stage gripping process. During the first stage, as the prehensor 30 moves from operating point A to operating point B on the graph 182, the prehensor is sizing the object. That is, the prehensor 30 is moving sizing digit 33 until the sizing digit 33 comes into contact with the object. Since the prehensor 30 is not yet applying a force directly to the object during the first stage, the wearer need only exert a small tension on the cable 34. When the prehensor 30 reaches the operating point B on the graph 182, the digits 32, 33 are in contact with the object to be grasped. The transition from operating point B to operating point C on the graph 182 illustrates the change between the end of the first stage and the beginning of the second stage. In order for the prehensor 30 to firmly grasp the object, the wearer must exert force against the object with the digits 32, 33 sufficient to fullly grasp the object with the digits 32, 33. A "full" grasp of an object means that the prehensor 30 has applied enough force against the object to enable lifting or manipulation of the object. The second stage of the gripping process for the prehensor 30 is between operating point C and operating point D on the graph 182, during which time force sufficient to fully grasp the object is created by the wearer.

The operation of the prehensor 30 will now be discussed in more detail, with particular reference to the graph 182 illustrated in FIG. 16. When the prehensor 30 is at operating point A in graph 182, the prehensor 30 is in its fully open position, as illustrated FIGS. 1–2, 4, and 12. A slight tension exists in the cable 34 exists as a result of the prehensor's 30 attachment to the wearer's harness. During the first stage, ie., as the operating point moves from operating point A to operating point B on the graph 182, the sizing digit 33 moves as a result of the tension applied to the cable 34 by the wearer.

When the wearer initiates a gripping cycle by applying tension to the cable 34, the tension in the cable is increased until the tension overcomes the initial bias force in the spring 138 which biases the position of the carriage block 108 on the lock rod 130. Until the tension in the cable 34 overcomes the spring bias against the carriage block 108, the carriage block 108 will not slide along the lock rod 130 and there is no displacement of the cable 34. Operating point A on the graph 182 is the operating point of the prehensor 30 where the tension in the cable 34 becomes high enough to overcome the bias against the carriage block 108 created by the spring 138 and to cause displacement of the cable 34.

Figures 17, 18:
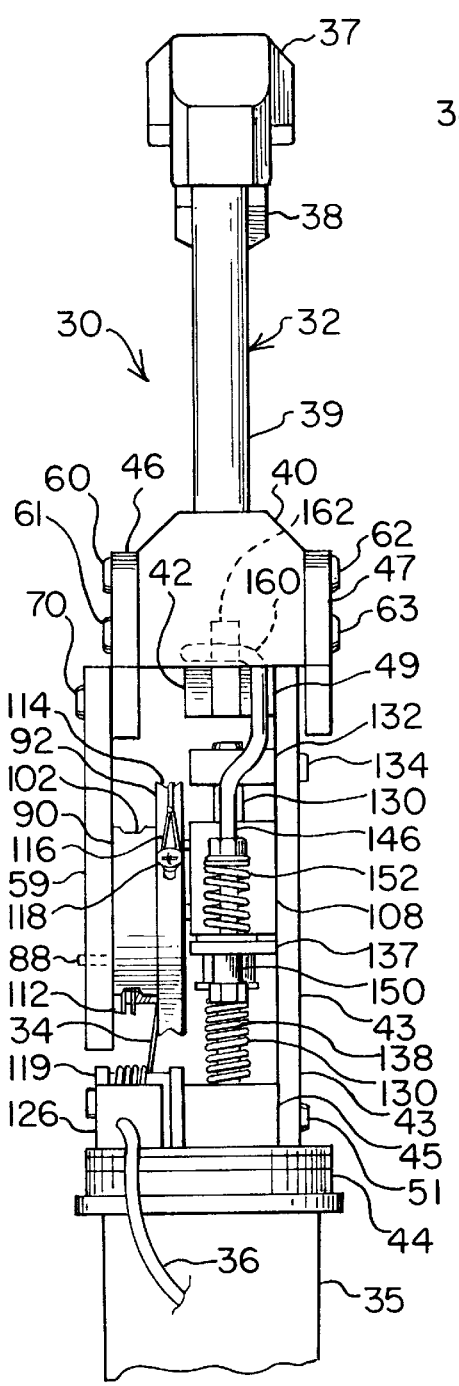
FIG. 17 illustrates a side elevation view of the prehensor of FIG. 1, with the prehensor shown during its initial sizing of an object to be grasped, just prior to contact between the prehensor and the object.
FIG. 18 illustrates a top plan view of the prehensor of FIG. 17.

After the tension in the cable 34 becomes high enough to overcome the bias in the carriage block 108 created by spring 138, as the wearer increases the tension in the cable 34, thereby increasing displacement of, and tension in, the cable 34, the carriage block 108 will slide or move along the lock rod 130 toward the circular end plate 44, as illustrated in FIGS. 10, and 17–18, and the prehensor 30 will begin moving from the operating point A on the graph 182 to the operating point B. The spring 138 will be compressed as the carriage block 108 moves along the lock rod 130 toward the circular end plate 44 and away from the stop block 132. The clutch drum 119 will rotate freely counterclockwise because of friction between the cable 34 and the clutch drum 119, thereby causing the cable 34 and the clutch drum 119 to behave like a simple pulley and preventing an unnecessary increase of tension in the cable 34. As the carriage block 108 slides along the lock rod 130, the carriage block 108 pushes the lock plate 137 along the lock rod 130 toward the circular end plate 44. The lock plate 137 will remain in its upright, i.e, non-tilted or non-skewed, position on the lock rod 130 and square against the carriage block 108, due to the force exerted against the lock plate 137 by the spring 138, until the digit blocks 37, 38 contact the object 31. As the lock plate 137 moves along the lock rod 130 and toward the circular end plate 44, the linkage rod 146 will be displaced toward the circular end plate 44, thereby causing the sizing block 42 to pivot or rotate clockwise (as viewed in FIG. 1) about the shaft 48 which will move the sizing digit 33 relative to the plate 43 and the gripping digit 32, as indicated by the direction arrow 183 in FIG. 17. During the sizing stage for the prehensor 30, the gripping digit 32 remains in a generally constant position relative to the structural plate 43.

Figure 19:
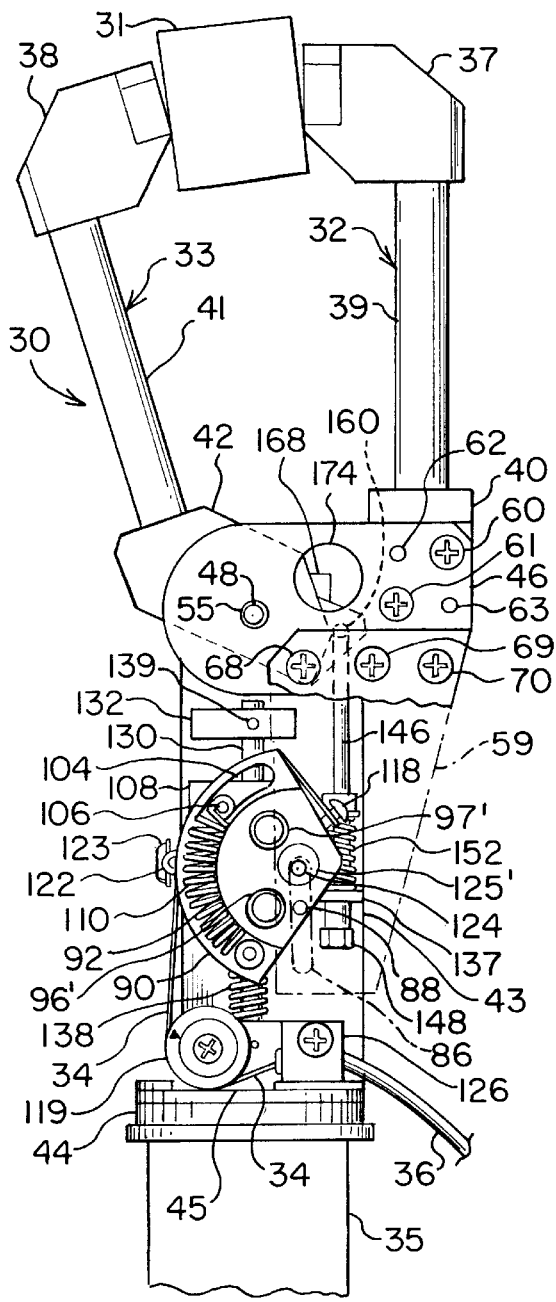
FIG. 19 illustrates a side elevation view of the prehensor of FIG. 1, with the prehensor shown after its initial gripping of an object after the prehensor has sized the object.
Figure 20:
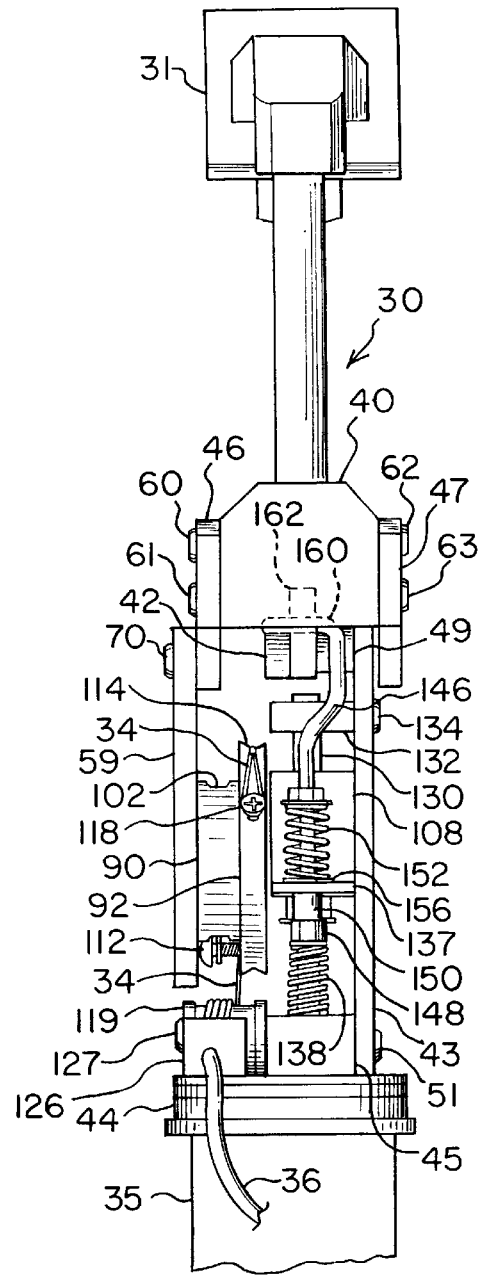
FIG. 20 illustrates a top plan view of the prehensor of FIG. 19.

Upon contact between the object 31 being grasped and the digit blocks 37, 38, the object 31 will exert a force against the digit blocks 37, 38, thereby preventing further movement or rotation of the sizing digit 33. This force will be passed through the linkage rod 146 to the lock plate 137, thereby causing resistance to sliding movement of the lock plate 137 along the lock rod 130 toward the circular end plate 44. More specifically, as previously discussed above, prior to the digit blocks 37, 38 contacting the object 31, increasing the tension in the cable 34 will cause the carriage block 108 to slide along the lock rod 130 toward the circular end plate 44. Movement or displacement of the carriage block 108 along the lock rod 130 towards the circular end plate 44 causes the lock plate 137 to slide or become displaced along the lock rod 130 towards the circular end plate 44, thereby creating a force on the linkage rod 146 that moves the linkage rod 146 towards the circular end plate 44. Movement or displacement of the linkage rod 146 towards the circular end plate 44 causes the sizing digit 33 to rotate or pivot about the shaft 48 until the object 31 is lightly gripped between the digit blocks 37, 38. A representative example of positions of the carriage block 108 and the lock plate 137 prior to the digit blocks 37, 38 contacting the object 31 is illustrated in FIG. 10. Once the object 31 has been gripped with or between the digit blocks 37, 38, the resistance force created by the object 31 against the digit blocks 37, 38 will prevent further rotation of the sizing digit 33 about the shaft 48, thereby preventing further movement of the linkage rod 146. Once movement or displacement of the linkage rod 146 is prevented, further tension on the cable 34 by the wearer will cause the carriage block 108 to slide along the lock rod 130 such that the force exerted by the carriage block 108 against the lock plate 137 causes the lock plate 137 to skew, tilt, or rotate about the lock rod 130, as illustrated in FIG. 11. Tilting or skewing of the lock plate 137 on the lock rod 130 will create a force between the lock plate 137 and the lock rod 130 such that the lock plate 137 cannot slide or become displaced along the lock rod 130. After the lock plate 137 tilts or skews about the lock rod 130 such that the lock plate 137 can no longer slide or be displaced along the lock rod 130 towards the circular end plate 44, the carriage block 44 will also be prevented from sliding or moving along the lock rod 130 towards the circular end plate 44, regardless of the increased tension exerted by the wearer with the cable 34. The cessation of sliding movement toward the circular end plate 44 of the lock plate 137 and the carriage block 108 on the lock rod 130 represents operating point B on the graph 182 of FIG. 16. The configuration of the prehensor 30 just prior to the operating point B is illustrated in FIGS. 17 and 18. The configuration of the prehensor 30 at the operating point B is illustrated in FIGS. 19 and 20.

Only after the prehensor 30 has appropriately sized the object 31 will the prehensor 30 allow the wearer to exert enough tension in the cable 34 to apply a force against the object 31 suitable for firmly or fully grasping the object 31. The movement from operating point B to operating point C on the graph 182 in FIG. 16 represents an increase in tension or displacement of the cable 34 created by the wearer to overcome the spring bias created by the spring 110 on the lower cam plate 92. Therefore, during the transition from operating point B to operating point C on the graph 182, there is very little, if any, motion within the prehensor 30 except for the cable 34 and the clutch drum 119. The clutch drum 119 will continue to rotate freely counterclockwise as the wearer exerts increased tension on the cable 34.

Once the wearer exerts force on the cable 34 sufficient to overcome the initial bias of the spring 110, the operating point C on the graph 182 for the prehensor 30 is reached. After the operating point C is reached, further tension on the cable 34 will cause the upper cam plate 90 and the lower cam plate 92 to rotate counterclockwise about the shaft 124, as best illustrated in FIG. 21. The increased tension on the cable 34 will also cause the cable 34 to move, thereby causing the clutch drum 119 to rotate further counterclockwise. Since the upper cam plate 90 and the lower cam plate 92 are rigidly connected together with the bolts 92, 94, as previously discussed above, the upper cam plate 90 and the lower cam plate 92 will rotate or pivot synchronously about the shaft 124. Increasing the tension on the cable 34 after the operating point C on the graph 182 is reached will move the prehensor 30 to operating point D on the graph 182, as will be discussed in more detail below. Since the wearer can control the amount of tension on the cable 34, the wearer controls the final position of the operating point D on the graph 182. Typically, the wearer will not want to exert unnecessary force against the object 31 when grasping the object 31, particularly if the object 31 is fragile or otherwise structurally weak. Therefore, the operating point D on the graph 182 is usually the point at which the wearer has created the minimum tension necessary on the cable 34 to apply sufficient grasping force against the object 31 with the digit blocks 37, 38, although in some cases the wearer may create more tension in the cable 34 than is necessary when grasping the object 31.

As the lower cam plate 92 rotates counterclockwise, the spring 110 extending between the movable bolt 112 and the stationary rod 106 will elongate. As previously discussed above, the bolt 112 is rigidly connected to the lower cam plate 92, such that the bolt 112 moves proportionally to the movement of the lower cam plate 92. The rod 106 is rigidly connected to the carriage block 108 (see FIGS. 10–11), however, such that the rod 106 does not move during the transition from the operating point C to the operating point D on the graph 182. Rather, during rotation of the lower cam plate 92, the rod 106 continuously extends through the slot 104 in the lower cam plate 92 and engages the spring 110, thereby creating tension or stretch in the spring 110 as the lower cam plate 92 rotates about the shaft 124. That is, during rotation of the cam plates 90, 92, the spring 110 elongates between the bolt 112 and the rod 106, which are connected to opposite ends of the spring 110, due to the movement of the bolt 112 in conjunction with the cam plates 90, 92 and the relatively stationary position of the rod 106.

As the upper cam plate 90 rotates about the shaft 124, the rod 88 rigidly connected to the upper cam plate 90 and extending through the slot 86 in the cam lever plate 59 exerts an upward force against the upper inside edge of the slot 86 in the lever plate 59. As previously discussed above, the lever plate 59 is rigidly connected to the pivot plate 46 with the bolts 68, 69, 70 and the pivot plate 46 is rigidly connected to the grip block 40 with the bolts 60, 61. Furthermore, the grip block 40 is rigidly connected to the pivot plate 47 with the bolts 62, 63. Both pivot plates 46, 47 and the grip block 40 can rotate about the shaft 48. With this rigid structural connection between the cam lever plate 59, the pivot plates 46, 47, and the grip block 40, when an upward force is created against the plate 59 by the rod 88 engaging the upper inside edge of the slot 86 in the plate 59, the cam lever plate 59, the pivot plates 46, 47, and the grip block 40 act in unison as a single structural element and rotate counterclockwise about the shaft 48, as best illustrated in FIG. 21. Since the sizing digit 33 is rigidly connected to the grip block 40, the sizing digit 33 moves or rotates counterclockwise, as indicated by the arrow 185 in FIG. 21, such that the digit block 38 moves closer to the digit block 37, thereby increasing the force exerted by the digit blocks 37, 38 against the object 31. Since the wearer can control the amount of tension exerted on the cable 34, the wearer can control the amount of force exerted against the object 31 with the prehensor 30 and, as a result, the position of the operating point D on the graph 182 shown in FIG. 16.

Extension of the spring 110 during rotation of the lower cam plate 92 creates a bias force against gripping of the object 31 such that when the wearer releases sufficient tension in the cable 34, the object 31 will not be grasped by the prehensor 30. The bias force created by elongation of the spring 110 enables the wearer to determine the correct tension in the cable 34 needed to grasp the object 31 and to maintain an awareness of the tension in the cable 34 necessary to maintain a grasp on the object 31. Thus, the prehensor 30 allows physiological prociprioception for the wearer.

After the wearer has applied sufficient tension against the cable 34 to grasp the object 31, the prehensor 30 preferably provides the capability of allowing the wearer to relax or reduce the tension on the cable 34 maintained by the wearer such that the wearer expends less energy or muscular effort while maintaining a grasp of the object 31. The movement from operating point D to operating point E on the graph 182 illustrates this capability. As the graph 182 illustrates, during movement from the operating point D to the operating point E, the tension force in the cable 34 created by the wearer is reduced. The displacement of the cable 34 is maintained, however, such that the prehensor 30 maintains the same grasp of the object 31.

The prehensor 30 allows the wearer to relax the tension in the cable 34 provided by the wearer, while maintaining a suitable tension on the cable 34, through use of the clutch drum 119. As previously discussed above, the clutch drum 119 preferably rotates only in a counterclockwise direction. Therefore, when the wearer is increasing tension on the cable 34 during movement of the operating point from operating point A to operating point B, during movement of the operating point from operating point B to operating point C, or during movement of the operating point from operating point C to operating point D, such that displacement of the cable 34 is increased, the clutch drum 119 rotates counterclockwise to facilitate such increase in cable 34 displacement. When the operating point moves from operating point D to operating point E, however, the wearer is reducing the tension in the cable 34 created by the wearer, the clutch drum does not rotate and, as a result, friction between the cable 34 and the clutch drum 119 is created that resists displacement of the cable 34. Thus, as the wearer reduces tension in the cable 34, friction between the clutch drum 119 and the cable 34 will help maintain tension in the cable 34 sufficient to grasp the object 119. While the wearer cannot completely reduce the tension in the cable 34 provided by the wearer, the use of the clutch drum 119 allows the wearer to significantly reduce the energy expended by the wearer to maintain a grasp on an object.

During movement from the operating point D to the operating point E on the graph 182, no movement of the components of the prehensor 30 occurs, except for possible movement of the cable 34. The operating point E on the graph 182 represents minimum tension required by the wearer to maintain a suitable grasp of the object 31. If the tension supplied on the cable 34 by the wearer falls below the operating point E, the cable 34 begins to slip around the clutch drum 119 and the prehensor 30 will no longer suitably grasp the object 31.

After the operating point E on the graph 182 is reached, further reduction by the wearer of tension applied against the cable 34 will move the operating point of the prehensor from the operating point E to the operating point F on the graph 182. During the movement from the operating point E to the operating point F on the graph 182, the upper cam plate 90 and the lower cam plate 92 will rotate clockwise about the shaft 124, thereby reducing elongation of the spring 110 until the rod 88 no longer applies an upward force against the upper inside edge of the slot 86 in the cam lever plate 59. When the operating point F on the graph 182 is reached, upper cam plate 90, the lower cam plate 92. the cam lever plate 59, the pivot plates 46, 47, and the rigid block 40 will return to their original position, as illustrated in FIG. 22. While the object 31 still appears to be grasped between the digit blocks 37, 38 in FIG. 22, the digit blocks 37, 38 are not exerting a significant force against the object 31. Usually, at the operating point F on the graph 182, the lock plate 137 remains in its tilted and locked position, and neither the lock plate 137 nor the carriage block 108 have yet moved along the lock rod 130 away from the circular end plate 44. During movement of the prehensor 30 from the operating point E to the operating point F, the clutch drum 119 will not rotate.

After the prehensor 30 has reached the operating point F, the lock plate 137 will still be in its tilted position as illustrated in FIG. 11. Further reduction in the tension applied against the cable 34 by the user will transition the prehensor 30 from the operating point F to the operating point G on the graph 182. During this transition stage, the carriage block 108 will not be forced towards the circular end plate 44 by tension in the cable 34. Therefore, the carriage block 108 will not be applying any force against the lock plate 137 biasing the lock plate 137 toward the circular end plate 44 and, as a result, no compression force will be applied against the spring 138 on the lock rod 130. When this happens, the spring 138 will "pop" loose or unskew or until the lock plate 137 so that the lock plate 137 will return to its non-skewed or non-tilted position on the lock rod 130 as illustrated in FIG. 10. During the transition from operating point F to operating point G on the graph 182, none of the other components of the prehensor 30 undergo any significant movement. During movement of the prehensor 30 from the operating point F to the operating point G on the graph 182, the clutch drum 119 will not rotate.

After the operating point G on the graph 182 is reached, a further reduction in the tension on the cable 34 will cause the carriage block 108 to move along the lock rod 130 away from the circular end plate 44 and towards the carriage stop block 132 as the spring 138 expands from its compressed position. In addition, expansion of the spring 138 will cause the lock plate 137 to move in conjunction with the carriage block 108 in a direction away from the circular end plate 44 and towards the stop block 132. As the lock plate 137 moves along the lock rod 130 away from the circular end plate 44, the lock plate 137 will cause the linkage rod 146 to move in the same direction, thereby causing the linkage rod 146 to create counter-clockwise rotation of the sizing digit 33 about the shaft 48 and moving the prehensor 30 to its fully open position illustrated by the operating point H on the graph 182. As illustrated by the previous discussion, the prehensor 30 does not require positive action by the wearer to disengage the prehensor 30 from the object 31. That is, if the wearer sufficiently reduces tension in the cable 34, the prehensor 30 will passively disengage itself from the object 31, without requiring positive action by the wearer. The passive disengagement feature of the prehensor 30 improves the safety of the prehensor 30 by preventing the prehensor 30 from "locking" onto any object without the active participatiorn of the wearer and by causing the prehensor 30 to automatically disengage from a grasped object when the wearer reduces tension in the cable 34.

The foregoing description is considered as illustrative only of the principles of the invention. Furthermore, since numerous modifications and changes will readily occur to those skilled in the art, it is not desired to limit the invention to the exact construction and process shown and described above. Accordingly, all suitable modifications and equivalents may be resorted to falling within the scope of the invention as defined by the claims which follow. For example, while the spring 110 is illustrated undergoing extension or tension during grasping of an object, the prehensor 30 could easily be modified such that a spring undergoes compression instead. Similarly, while the springs 138 and 152 are illustrated in compression during grasping of an object, either or both of the springs could easily be modified such that they undergo extension instead of compression. In addition, combinations of two or more springs may also be used to achieve each of these functions. As another example of possible modifications to the prehensor 30, the size and shape of the digit blocks 37, 38 can be tailored for specific applications, for grasping specific objects, or for grasping objects of a specific configuration. Furthermore, while the pivot plates 43, 46, 47, and 49, along with the size block 42 are all attached to or rotate around a single shaft 48, multiple shafts could be used such that the pivot plates 46, 47 rotate about one shaft while the size block 42 rotates about a different shaft, which may increase the mechanical operation or efficiency of the prehensor 30. As another example, the plates 46, 47, 59 and the grip block 40 essentially form a grip block assembly that rotates about the shaft 48. Obviously, the sizes and shapes of the plates and block of the grip block assembly and, in fact, the entire prehensor 30, can be modified or tailored and the present invention should not be limited. only to the shapes and sizes of the blocks and plates illustrated herein. While the plates and blocks of the prehensor 30 preferably comprise a metal material, such as steel or aluminum, other materials can also be used. As reduction of the weight of the prehensor 30 may be a concern in some applications, all of the plates and blocks of the prehensor 30 can be modified such that the weight of the prehensor 30 is reduced while the prehensor 30 simultaneously maintains a strong or rigid structure. As another example of possible modifications to the prehensor 30, instead of rotatably connecting the cam plates 90, 92 to the carriage block 108, the cam plates 90, 92 can be positioned to the carriage block such that the cam plates 90, 92 are not necessarily displaced when the carriage block slides or becomes displaced along the lock rod 130. Alternatively, the cam plates 90, 92 can be displaced when the carriage block 108 is displaced without being connected directly to the carriage block 108. Furthermore, while the plates and blocks of the prehensor 30 preferably comprise metal, such as steel or aluminum, any or all of the plates or blocks can comprise other materials. In addition, while the plates and blocks are illustrated as being primarily connected via bolts, the plates and blocks can be connected via welding, brazing, gluing, or other suitable means.

The embodiments of the invention in which an exclusive property or privilege is claimed are defined as follows:

1. A cable actuated prehensor for grasping an object, comprising:
   a carriage block displaceable along a lock rod, said carriage block coupled to a rotatable sizing digit such that displacement of said carriage block alone said lock rod causes rotation of said sizing digit, said sizing digit being connected to a main structural plate; and
   a rotatable cam plate having a displaceable axis of rotation, said cam plate coupled to said carriage block such that displacement of said carriage block along said lock rod displaces said axis of rotation of said cam plate, said cam plate also being coupled to a rotatable gripping digit such that rotation of said cam plate about said axis of rotation causes rotation of said gripping digit, said gripping digit being connected to said main structural plate.

2. The prehensor of claim 1, wherein said coupling between said carriage block and said sizing digit includes a lock plate slidable along said lock rod.

3. The prehensor of claim 2, wherein said lock plate is biased such that as said carriage block is displaced along said lock rod, said lock plate is also displaced along said lock rod.

4. The prehensor of claim 3, wherein said lock plate is biased by a spring.

5. The prehensor of claim 4, wherein said lock rod extends through said spring.

6. The prehensor of claim 2, wherein said lock plate is skewable about said lock rod such that when said lock plate is not skewed about said lock rod, said lock plate is slidable along said lock rod and when said lock plate is skewed about said lock rod, said lock plate is not slidable along said lock rod.

7. The prehensor of claim 6, wherein when said lock plate is not slidable along said lock rod, said carriage block is also not slidable along said lock rod.

8. The prehensor of claim 6, wherein said lock plate becomes skewed about said lock rod when said sizing digit rotates to the point that said sizing digit and said gripping digit are in contact with the object.

9. The prehensor of claim 2, wherein said lock rod extends through said lock plate.

10. The prehensor of claim 9, wherein said lock rod extends through said carriage block.

11. The prehensor of claim 2, wherein said coupling between said carriage block and said sizing digit includes a linkage rod connecting said lock plate and said sizing digit.

12. The prehensor of claim 1, including a cable coupled to said plate and a rotatable drum around which the cable is wound at least one complete revolution.

13. The prehensor of claim 12, wherein said drum is rotatable in either a clockwise direction or in a counter-clockwise direction but not both.

14. The prehensor of claim 12, wherein said drum rotates only when tension in the cable is increased.

15. The prehensor of claim 12, wherein friction between said drum and the cable assists in maintaining tension in the cable.

16. The prehensor of claim 1, including a cable connected to said rotatable plate and a holding assist device coupled to said cable and capable of applying tension to said cable.

17. The prehensor of claim 16, wherein said holding assist device includes a clutched cylinder around which said cable is wound.

18. The prehensor of claim 17, wherein said clutched cylinder rotates when tension in said cable is increased.

19. A cable actuated prehensor, comprising:
 a rotatable sizing digit rotatable coupled to a main structural plate and mechanically coupled to a cable, wherein said sizing digit rotates when tension in the cable is increased from below a first tension level to said first tension level;
 a rotatable gripping digit mechanically coupled to the cable and rotatably coupled to said main structural plate, wherein said gripping digit rotates when tension in the cable is increased from a second tension level to tension level higher than said second tension level, said second tension level being higher than said first tension level; and
 a rotatable drum around which the cable is wound at least one complete revolution, said drum being rotatable coupled to said main structural plate, wherein said drum is rotatable in either a clockwise direction or in a counter-clockwise direction but not both.

20. The prehensor of claim 19, wherein said drum rotates only when cable tension is increased.

21. The prehensor of claim 19, wherein friction between said drum and the cable assists in maintaining tension in the cable.

22. The prehensor of claim 19, wherein said mechanical coupling between said sizing digit and the cable includes a displaceable carriage block and a cam plate rotatably connected to said carriage block such that displacement of said carriage block also displaces said cam plate, wherein the cable is connected to said cam plate.

23. The prehensor of claim 22, wherein said gripping digit is mechanically coupled to said cam plate such that rotation of said cam plate causes rotation of said gripping digit.

24. The prehensor of claim 22, wherein said carriage block is mechanically coupled to said sizing digit such that displacement of said carriage block causes rotation of said sizing digit.

25. The prehensor of claim 22, including a lock rod along which said carriage block is displaceable.

26. The prehensor of claim 25, including a lock plate slidable along said lock rod and mechanically coupled to said sizing digit.

27. The prehensor of claim 26, wherein said lock plate is skewable about said lock rod such that when said lock plate is not skewed about said lock rod, said lock plate is slidable along said lock rod, and when said lock plate is skewed about said lock rod, said lock plate is not slidable along said lock rod.

28. The prehensor of claim 27, wherein said lock plate is not skewed about said lock rod when cable tension is less than said first cable tension level.

29. The prehensor of claim 28, wherein said lock plate is skewed about said lock rod when said cable tension is greater than said second cable tension level.

30. A prehensor, comprising:
 a sizing digit rotatably connected to a main structural plate;
 a gripping digit rotatable connected to said main structural plate;
 a lock rod coupled to said main structural plate;
 a carriage block that is slidable along said lock rod and coupled to said sizing digit such that displacement of said carriage block along said lock rod causes rotation of said sizing digit; and
 a rotatable cam plate having an axis of rotation and coupled to said gripping digit via a lever plate such that rotation of said cam plate causes rotation of said gripping digit, wherein said rotatable cam plate is also coupled to said carriage block such that displacement of said carriage block along said lock rod displaces said axis of rotation of said rotatable cam plate.

31. The prehensor of claim 30, including a lock plate positioned along said lock rod and adjacent said carriage block such that said carriage block is not displaceable along said lock rod while said rotatable cam plate is rotating about said axis of rotation of said rotatable cam plate.

32. The prehensor of claim 30, wherein said rotatable cam plate does not rotate about said axis of rotation while said carriage block is being displaced along said lock rod.

* * * * *